(12) United States Patent
Koyama

(10) Patent No.: US 9,044,748 B2
(45) Date of Patent: Jun. 2, 2015

(54) CARTRIDGE

(71) Applicants: CANON MARKETING JAPAN KABUSHIKI KAISHA, Tokyo (JP); ELK CORPORATION, Osaka (JP); KABUSHIKI KAISHA ELQUEST, Chiba (JP)

(72) Inventor: Takashi Koyama, Tokyo (JP)

(73) Assignees: CANON MARKETING JAPAN KABUSHIKI KAISHA, Tokyo (JP); ELK CORPORATION, Osaka (JP); KABUSHIKI KAISHA ELQUEST, Chiba (JP)

( * ) Notice: Subject to any disclaimer, the term of this patent is extended or adjusted under 35 U.S.C. 154(b) by 0 days.

(21) Appl. No.: 13/645,174

(22) Filed: Oct. 4, 2012

(65) Prior Publication Data
US 2013/0095010 A1    Apr. 18, 2013

(30) Foreign Application Priority Data

Oct. 6, 2011   (JP) .................................. 2011-222384
Jun. 29, 2012  (JP) .................................. 2012-147388

(51) Int. Cl.
  *G01N 33/00*   (2006.01)
  *B01L 3/00*    (2006.01)
  *A61L 2/18*    (2006.01)

(52) U.S. Cl.
  CPC . *B01L 3/00* (2013.01); *A61L 2/186* (2013.01);
  *A61L 2202/11* (2013.01); *A61L 2202/121* (2013.01); *A61L 2202/15* (2013.01); *A61L 2202/13* (2013.01); *A61L 2202/182* (2013.01)

(58) Field of Classification Search
  CPC ..................... A61L 2202/11; A61L 2202/121; A61L 2202/13; A61L 2202/15; A61L 2202/182; A61L 2/186; B01L 3/00
  USPC .......................... 422/400, 401, 500, 513, 554
  See application file for complete search history.

(56) References Cited

U.S. PATENT DOCUMENTS 6,723,568 B1 *   4/2004   Liu et al. ....................... 436/174

FOREIGN PATENT DOCUMENTS

| EP | 1010640 A | 6/2000 |
|----|-----------|--------|
| JP | 2003-200971 A | 7/2003 |
| JP | 3100971 U | 6/2004 |
| JP | 2006-158958 A | 6/2006 |

* cited by examiner

*Primary Examiner* — Sam P Siefke
(74) *Attorney, Agent, or Firm* — Canon USA, Inc. IP Division

(57) ABSTRACT

A cartridge capable of storing a chemical solution includes a first container, a second container installed within the first container and configured to store the chemical solution, and an exhaust path configured to exhaust a gas generated by the chemical solution stored in the second container, wherein the exhaust path is disposed between the first container and the second container.

15 Claims, 12 Drawing Sheets

<CROSS-SECTIONAL VIEW OF CROSS-SECTION 1>

<REAR SURFACE OF A SEAL WHEN THE CROSS-SECTION 2
IS VIEWED FROM THE LOWER SIDE OF THE CARTRIDGE>

<CROSS-SECTIONAL VIEW OF THE CROSS-SECTION 2
VIEWED FROM THE UPPER SIDE OF THE CARTRIDGE>

<CROSS-SECTIONAL VIEW OF THE CROSS-SECTION 3
VIEWED FROM THE UPPER SIDE OF THE CARTRIDGE>

<CROSS-SECTIONAL VIEW OF THE CROSS-SECTION 4
VIEWED FROM THE UPPER SIDE OF THE CARTRIDGE>

<CROSS-SECTIONAL VIEW OF THE CROSS-SECTION 5
VIEWED FROM THE UPPER SIDE OF THE CARTRIDGE>

<CROSS-SECTIONAL VIEW OF CROSS-SECTION 1>

<REAR SURFACE OF A SEAL WHEN THE CROSS-
SECTION 2 IS VIEWED FROM THE LOWER SIDE
OF THE CARTRIDGE>

CARTRIDGE

BACKGROUND OF THE INVENTION

1. Field of the Invention

One disclosed aspect of the embodiments relates to a cartridge.

2. Description of the Related Art

Sterilization apparatuses for sterilizing an object for sterilization such as a medical instrument have been conventionally used, for example, in the medical field. Such a sterilization apparatus evaporates hydrogen peroxide or a hydrogen peroxide solution as a sterilizing agent, and sterilizes an object for sterilization by bringing the object for sterilization into contact with the evaporated hydrogen peroxide.

Conventionally, a dose of a sterilizing agent used in a sterilization apparatus is absorbed by the sterilization apparatus from a cassette including a plurality of cells each containing a dose of the sterilizing agent to be used to sterilize an object for sterilization (for example, Japanese Patent Application Laid-Open No. 2006-158958).

An amount of sterilizing agent which may be evaporated is determined according to a capacity of a sterilization chamber, and thus an amount of sterilizing agent used in sterilizing processing is determined according to the capacity of the sterilization chamber. In addition, conventionally, a capacity of a sterilization chamber may be different according to the types of sterilization apparatuses. Therefore, when a plurality of types of sterilization apparatuses whose sterilization chambers have different capacities is used, sterilizing agent cassettes suitable for the respective sterilization apparatuses are necessary. More specifically, amounts of sterilizing agents to be used in the sterilization apparatuses are different, and cassettes used in the respective sterilization apparatuses need to be prepared, thus the cassettes are not common and the costs for purchasing the respective cassettes are necessary.

It is considered to use a cartridge where one bottle contains a sterilizing agent with sufficient amount suitable for a plurality of types of sterilizing processing. However, when such a cartridge is used, an amount of liquid sterilizing agent (for example, a hydrogen peroxide solution) which may be contained in the cartridge becomes larger, and thus an air pressure in the cartridge becomes higher due to water or oxygen gas generated when hydrogen peroxide in the cartridge is discomposed while the cartridge is stored, making a possibility of damaging the cartridge or leaking a liquid higher. Further, if the cartridge is damaged, for example, due to a drop of the cartridge, a possibility of leaking a liquid sterilizing agent in the cartridge becomes higher.

SUMMARY OF THE INVENTION

One disclosed aspect of the embodiments is directed to a cartridge capable of reducing a possibility of leaking a chemical solution from a cartridge in which the chemical solution is stored.

According to an aspect of the embodiments, a cartridge capable of storing a chemical solution includes a first container, a second container installed within the first container and configured to store the chemical solution, and an exhaust path configured to exhaust a gas generated by the chemical solution stored in the second container, wherein the exhaust path is disposed between the first container and the second container.

Further features and aspects of the disclosure will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the disclosure and, together with the description, serve to explain the principles of the disclosure.

DESCRIPTION OF THE EMBODIMENTS

Various exemplary embodiments, features, and aspects of the disclosure will be described in detail below with reference to the drawings.

First Exemplary Embodiment

A first exemplary embodiment of a sterilizing agent cartridge used in a sterilization apparatus will be described below with reference to the accompanying drawings.

Figure 1:
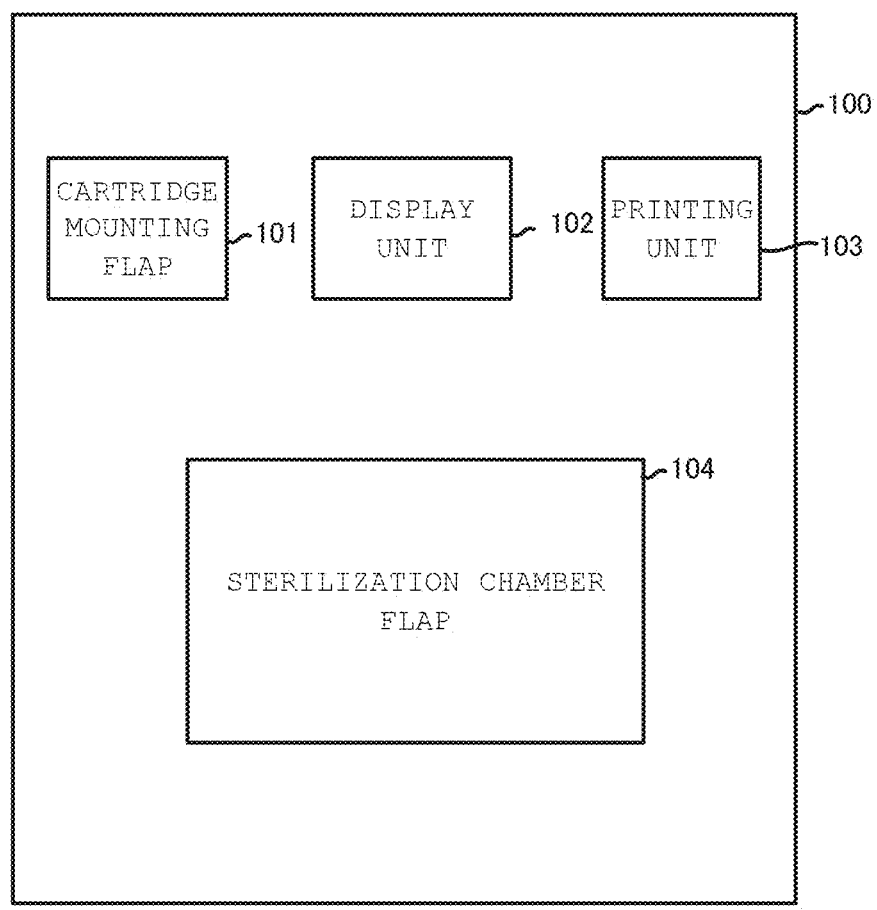
FIG. 1 illustrates an external appearance of a sterilization apparatus according to one embodiment when viewed from the front side.

First, an external appearance of the sterilization apparatus in which the sterilizing agent cartridge is installed will be described with reference to FIG. 1. FIG. 1 is a front view of the external appearance of the sterilization apparatus in which the sterilizing agent cartridge is installed. A sterilization apparatus 100 includes a cartridge mounting flap 101, a display unit 102, a printing unit 103, and a sterilization chamber flap 104.

The cartridge mounting flap 101 is a flap for mounting a cartridge which is a container filled with (storing) a sterilizing agent (for example, hydrogen peroxide or a hydrogen peroxide solution liquid). When the cartridge mounting flap 101 is opened, there is a cartridge mounting place, and a user may mount the cartridge therewith.

The display unit 102 is a touch panel display screen such as a liquid crystal display. The printing unit 103 is a printer which prints a history of sterilization processes and sterilization results on printing paper as appropriate.

The sterilization chamber flap 104 is a flap for inserting, for example, a target object for sterilization (object for sterilization) such as a medical instrument into a sterilization chamber to sterilize the objects for sterilization. When the sterilization chamber flap 104 is opened, there is the sterilization chamber, and the objects for sterilization may be inserted thereinto. When, the sterilization chamber flap 104 is closed, the target object for sterilization may be placed in the sterilization chamber and an interior of the sterilization chamber may be sealed.

The sterilization chamber is a housing with a predetermined capacity. An air pressure in the sterilization chamber may be maintained at the atmospheric pressure to a vacuum pressure. In addition, a temperature in the sterilization chamber is maintained at a temperature within a predetermined range during the sterilizing processing.

Figure 2:
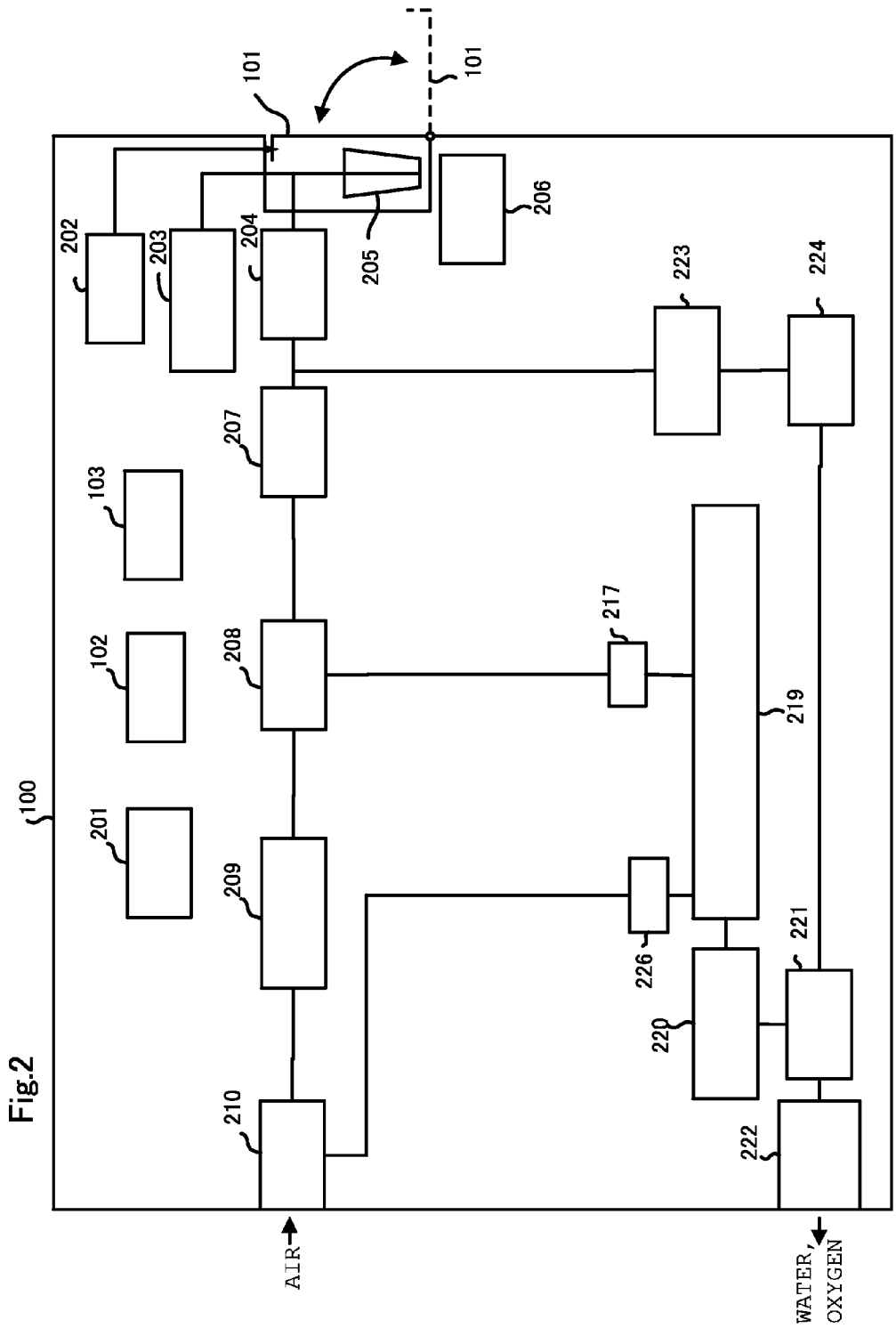
FIG. 2 illustrates an example of a hardware configuration of a sterilization apparatus according to one embodiment.

Next, an example of a hardware configuration of the sterilization apparatus in which the sterilizing agent cartridge is installed will be described with reference to FIG. 2. FIG. 2 illustrates the example of the hardware configuration of the sterilization apparatus in which the sterilizing agent cartridge is installed.

The sterilization apparatus 100 includes a computation processing unit 201 (a micro-processing unit (MPU) and the like), the display unit 102, the printing unit 103, a locking operation control unit 202, an extraction needle operation control unit 203, the sterilization chamber flap 104, a liquid sensor 204, a cartridge 205, a radio-frequency identification (RF-ID) reader/writer 206, a liquid transfer rotary pump 207, a preparation chamber 208, an air transfer pressure pump 209, an intake high efficiency particulate air (HEPA) filter 210, a valve (V5) 217, a valve (V7) 226, a sterilization chamber (also referred to as a vacuum chamber) 219, an air transfer vacuum pump 220, an exhaust HEPA filter 221, a sterilizing agent decomposition apparatus 222, a liquid transfer rotary pump 223, and an exhaust evaporation furnace 224.

The computation processing unit 201 (an MPU and the like) performs calculation processing and controls each hardware constituting the sterilization apparatus 100.

The display unit 102, the printing unit 103, and the cartridge mounting flap 101 are described above with reference to FIG. 1, and thus a detailed description thereof will be omitted here.

The locking operation control unit 202 is a unit for performing locking and unlocking operations of the cartridge mounting flap 101. When the cartridge mounting flap 101 is locked, the cartridge mounting flap 101 is prevented from being opened, and when the cartridge mounting flap 101 is unlocked, the cartridge mounting flap 101 is allowed to be opened.

The cartridge 205 is a sealed container filled with a sterilizing agent (hydrogen peroxide or a hydrogen peroxide solution liquid). In addition, an RF-ID storage medium is disposed at a lower side of the cartridge 205, and the storage medium stores a serial number as information for identifying the cartridge, a manufacturing date of the cartridge, a date and time (initial use date and time) when the cartridge is used in the sterilization apparatus for the first time, and a residual amount of the sterilizing agent filled in the cartridge.

The extraction needle operation control unit 203 is a unit for operating an extraction needle (injection needle) for suctioning the sterilizing agent in the cartridge to insert the extraction needle into an upper portion of the cartridge. In other words, the extraction needle is a straw (thin tube) for suctioning the sterilizing agent.

When the extraction needle (injection needle) for suctioning the sterilizing agent in the cartridge is inserted into the upper portion of the cartridge, the extraction needle (injection needle) may be inserted into the upper portion of the cartridge by lowering the extraction needle (injection needle) toward the cartridge from the upper portion thereof. When the extraction needle (injection needle) is withdrawn from the cartridge, the extraction needle (injection needle) may be withdrawn from the cartridge by raising the extraction needle (injection needle) at the upper portion of the cartridge.

The liquid sensor 204 is a unit for detecting whether the liquid sterilizing agent in the cartridge 205 is passing through the liquid transfer rotary pump 207 and a pipe (conduit pipe) communicated with the liquid transfer rotary pump 223 from the extraction needle (injection needle). More specifically, the liquid sensor 204 detects whether the sterilizing agent is passing through the pipe from a spectrum obtained by irradiating an infrared ray to the pipe.

The RF-ID reader/writer 206 is a unit capable of reading out a serial number, a manufacturing date, an initial use date and time, and a residual amount of the sterilizing agent from an RF-ID disposed at the lower side of the cartridge 205. In addition, the RF-ID reader/writer 206 is a unit capable of writing the initial use date and time and the residual amount of the sterilizing agent in the RF-ID disposed at the lower side of the cartridge 205.

The RF-ID reader/writer 206 is installed at a lower portion of the cartridge mounting location behind the cartridge mounting flap 101, and may read out the RF-ID disposed at the lower side of the cartridge 205 and write data such as the initial use date and time, the residual amount of the sterilizing agent, and the like in the RF-ID.

The liquid transfer rotary pump 207 is communicated with the preparation chamber 208 via a conduit pipe and is communicated with the liquid sensor 204 via a conduit pipe. The liquid transfer rotary pump 207 is a unit for suctioning the liquid sterilizing agent in the cartridge 205 with a pump and sending the sterilizing agent to the preparation chamber 208 via a conduit pipe. In addition, the liquid transfer rotary pump 207 may suction a predetermined amount of sterilizing agent from the cartridge 205 in association with the liquid sensor 204.

The preparation chamber 208 is communicated with the liquid transfer rotary pump 207, the air transfer pressure pump 209, and the sterilization chamber 219 via conduit pipes, respectively. The preparation chamber 208 is a space for preparing the sterilizing agent to control a timing for sending the sterilizing agent which is sent from the liquid transfer rotary pump 207 via the conduit pipe before the sterilizing agent is sent to the sterilization chamber (vacuum chamber) 219. A valve (V5) 217 is installed in a conduit pipe between the preparation chamber 208 and the sterilization chamber 219.

The air transfer pressure pump 209 is communicated with the preparation chamber 208 and the intake HEPA filter 210 via conduit pipes, respectively. The air transfer pressure pump 209 is a unit for communicating with the intake HEPA filter 210 via a conduit pipe and sending ambient air (air) of the sterilization apparatus 100 to the preparation chamber 208 via the intake HEPA filter 210.

The intake HEPA filter 210 is communicated with the air transfer pressure pump 209 and the sterilization chamber 219 via conduit pipes, respectively. The intake HEPA filter 210 cleans air by filtering out dust, specks, germs, and the like in the ambient air (air) outside the sterilization apparatus 100 with an HEPA filter. The cleaned air passes through a conduit pipe to be sent to the preparation chamber 208 by the air transfer pressure pump 209. In addition, the cleaned air passes through a conduit pipe with the sterilization chamber 219 to be sent into the sterilization chamber 219.

More specifically, the intake HEPA filter 210 is communicated with the ambient air (air) outside the sterilization apparatus 100. Therefore, a conduit pipe between the air transfer pressure pump 209 and the intake HEPA filter 210 and a conduit pipe between the sterilization chamber 219 and the intake HEPA filter 210 are communicated with the ambient air (air) via the intake HEPA filter 210. The valve (V7) 226 is disposed in a conduit pipe between the intake HEPA filter 210 and the sterilization chamber 219.

The valve (V5) 217 is a valve disposed in a conduit pipe between the preparation chamber 208 and the sterilization chamber 219. When the valve (V5) is opened, the preparation chamber 208 and the sterilization chamber 219 may be communicated with each other via the conduit pipe, and as the valve (V5) is closed, the preparation chamber 208 and the sterilization chamber 219 are prevented from being communicated with each other via the conduit pipe.

The valve (V7) 226 is a valve disposed in the conduit pipe between the sterilization chamber 219 and the intake HEPA filter 210. When the valve (V7) is opened, the sterilization chamber 219 and the intake HEPA filter 210 may be communicated with each other via the conduit pipe, and as the valve (V7) is closed, the sterilization chamber 219 and the intake HEPA filter 210 are prevented from being communicated with each other via the conduit pipe. In other words, the valve (V7) 226 is a valve capable of opening and closing the communication of the sterilization chamber 219 and the ambient air (air).

As described above with reference to FIG. 1, the sterilization chamber (also referred to as a vacuum chamber) 219 is a housing with a predetermined capacity for sterilizing a target object for sterilization, for example, a medical instrument and the like. The air pressure in the sterilization chamber may be maintained at the atmospheric pressure to a vacuum pressure. In addition, the temperature in the sterilization chamber is maintained at a temperature within a predetermined range during the sterilizing processing. Further, a pressure sensor is installed in the sterilization chamber 219, and a pressure (air pressure) in the sterilization chamber 219 may be measured by the pressure sensor. The sterilization apparatus 100 determines whether a pressure (air pressure) in the sterilization chamber 219 is a predetermined atmospheric pressure based on the pressure in the sterilization chamber 219 measured by the pressure sensor.

The air transfer vacuum pump 220 is a unit for suctioning the gas in the space of the sterilization chamber 219 to reduce the pressure therein and maintain the space in a vacuum state (a state in the space filled with a gas at a pressure lower than the atmospheric pressure). The air transfer vacuum pump 220 is communicated with the sterilization chamber 219 via a conduit pipe, and is communicated with the exhaust HEPA filter 221 via a conduit pipe.

The exhaust HEPA filter 221 is communicated with the air transfer vacuum pump 220 via the conduit pipe. The exhaust HEPA filter 221 is also communicated with the exhaust evaporation furnace 224 via a conduit pipe. Further, the exhaust HEPA filter 221 is communicated with the sterilizing agent decomposition apparatus 222 via a conduit pipe. Furthermore, the exhaust HEPA filter 221 is communicated with the preparation chamber 208 via a conduit pipe.

The exhaust HEPA filter 221 cleans the suctioned gas by filtering out dust, fine specks, germs, and the like in the gas which is suctioned from the sterilization chamber 219 by the air transfer vacuum pump 220 and sent via the conduit pipe by the HEPA filter. The cleaned gas is sent to the sterilizing agent decomposition apparatus 222 via a conduit pipe between the sterilizing agent decomposition apparatus 222 and the exhaust HEPA filter 221. The molecules of the sterilizing agent contained in the gas are decomposed by the sterilizing agent decomposition apparatus 222, and the decomposed molecules are emitted to the outside of the sterilization apparatus 100.

The exhaust HEPA filter 221 cleans the evaporated sterilizing agent sent from the exhaust evaporation furnace 224 via a conduit pipe between the exhaust evaporation furnace 224 and the exhaust HEPA filter 221. The cleaned sterilizing agent (gas) is sent to the sterilizing agent decomposition apparatus 222 via the conduit pipe between the sterilizing agent decomposition apparatus 222 and the exhaust HEPA filter 221. The molecules of the sterilizing agent contained in the gas are decomposed by the sterilizing agent decomposition apparatus 222, and the decomposed molecules are emitted to the outside of the sterilization apparatus 100.

The sterilizing agent decomposition apparatus 222 is communicated with the exhaust HEPA filter 221 via the conduit pipe. The sterilizing agent decomposition apparatus 222 decomposes the molecules of the sterilizing agent contained in the gas sent from the conduit pipe between the sterilizing agent decomposition apparatus 222 and the exhaust HEPA filter 221, and emits the molecules generated by the decomposition to the outside of the sterilization apparatus 100. The sterilizing agent decomposition apparatus 222 is an apparatus capable of decomposing the evaporated hydrogen peroxide into water and oxygen by using manganese dioxide as a catalyst, for example, when the sterilizing agent is hydrogen peroxide or a hydrogen peroxide solution.

The liquid transfer rotary pump 223 is communicated with the exhaust evaporation furnace 224 via a conduit pipe and is also communicated with the liquid sensor 204 via a conduit pipe. The liquid transfer rotary pump 223 is a unit for suctioning all the liquid sterilizing agent in the cartridge 205 with a pump, and sending all the sterilizing agent sent via the conduit pipe between the liquid sensor 204 and the liquid transfer rotary pump 223 to the exhaust evaporation furnace 224 via the conduit pipe between the liquid transfer rotary pump 223 and the exhaust evaporation furnace 224.

The exhaust evaporation furnace 224 is communicated with the liquid transfer rotary pump 223 via the conduit pipe and is communicated with the exhaust HEPA filter 221 via a conduit pipe. The exhaust evaporation furnace 224 heats all the liquid sterilizing agent in the cartridge 205 which is sent via the conduit pipe between the liquid transfer rotary pump 223 and the exhaust evaporation furnace 224 with a heater disposed in the exhaust evaporation furnace 224, and evaporates all the sterilizing agent. The evaporated sterilizing agent is sent to the exhaust HEPA filter 221 via the conduit pipe between the exhaust HEPA filter 221 and the exhaust evaporation furnace 224.

In this way, in the sterilization apparatus 100, when the sterilizing agent stored in the cartridge 205 is discarded, the liquid transfer rotary pump 223 suctions the sterilizing agent stored in the cartridge 205, and the sterilizing agent is introduced into the exhaust evaporation furnace 224, evaporated by the exhaust evaporation furnace 224, and sent to the exhaust HEPA filter 221. Then, the sterilization apparatus 100 decomposes the gas (sterilizing agent) cleaned by the exhaust HEPA filter 221 by the sterilizing agent decomposition apparatus 222, and emits the produced water and oxygen to the outside. Accordingly, the sterilizing agent stored in the cartridge 205 may be discarded.

The sterilization apparatus 100 reads out a serial number as information for identifying the cartridge, a manufacturing date of the cartridge, a date and time (initial use date and time) when the cartridge is used in the sterilization apparatus for the first time, and a residual amount of sterilizing agent filled in the cartridge from the RF-ID storage medium located at the lower side of the cartridge 205, and determines whether all the sterilizing agent stored in the cartridge 205 is to be discarded. When it is determined that the sterilizing agent is discarded, the sterilization apparatus 100 performs the above-described discarding processing.

For example, when a predetermined period of time elapses from the manufacturing date of the cartridge filled with the sterilizing agent, a sterilizing effect may not be sufficiently obtained from the sterilizing agent in the cartridge. Thus, the sterilization apparatus 100 performs processing for discarding the sterilizing agent in the cartridge if the predetermined period of time has elapsed from the manufacturing date of the cartridge filled with the sterilizing agent.

In addition, when a predetermined period of time elapses from a date and time (initial use date and time) when the cartridge filled with the sterilizing agent is used for the first time, a sterilizing effect may not be sufficiently obtained from the sterilizing agent in the cartridge. Thus, the sterilization apparatus 100 performs processing of discarding the sterilizing agent in the cartridge if the predetermined period of time has elapsed from the date and time (initial use date and time) when the cartridge filled with the sterilizing agent was used for the first time.

If the extraction needle (thin tube) is inserted into the cartridge to extract the sterilizing agent in the cartridge, a material promoting decomposition of the sterilizing agent may be mixed in and promote decomposition of the sterilizing agent. Therefor, the sterilization apparatus 100 performs processing for discarding the sterilizing agent in the cartridge if the predetermined period of time has elapsed from the date and time (initial use date and time) when the cartridge filled with the sterilizing agent is used in the sterilization apparatus for the first time.

In addition, when a residual amount of the sterilizing agent filled in the cartridge is less than a dose for the sterilizing processing, the sterilizing processing using the sterilizing agent in the cartridge may not be performed. Thus, the sterilization apparatus 100 performs processing for discarding the sterilizing agent in the cartridge when the residual amount of the sterilizing agent filled in the cartridge is less than the dose for the sterilizing processing.

All the valves in the sterilization apparatus 100 in which the sterilizing agent cartridge is installed remain closed when the sterilizing processing starts.

If the sterilizing processing starts, the sterilization apparatus in which the sterilizing agent cartridge is installed suctions the sterilizing agent (hydrogen peroxide solution) in the cartridge 205 and introduces the sterilizing agent into the preparation chamber 208 by the liquid transfer rotary pump 207.

At a timing when the preparation is completed (i.e., a timing when a pressure in the sterilization chamber 219 is reduced to a predetermined pressure by the air transfer vacuum pump 220), the valve (V5) 217 is opened and the sterilizing agent in the preparation chamber 208 is introduced into the sterilization chamber 219, so that the sterilizing agent is evaporated. The evaporated sterilizing agent contacts and sterilizes a target object for sterilization placed in the sterilization chamber 219.

When the valve (V7) 226 is opened, the ambient air is introduced into the sterilization chamber 219 via the intake HEPA filter 210.

Accordingly, a large amount of evaporated sterilizing agent is introduced into a cavity of the target object for sterilization, and thus an effect of the sterilizing action on the cavity may be increased. Then, the gas in the sterilization chamber 219 is suctioned by the air transfer vacuum pump 220, sent to the sterilizing agent decomposition apparatus 222 via the exhaust HEPA filter 221, and decomposed into water and oxygen to be emitted to the outside.

Figure 3:
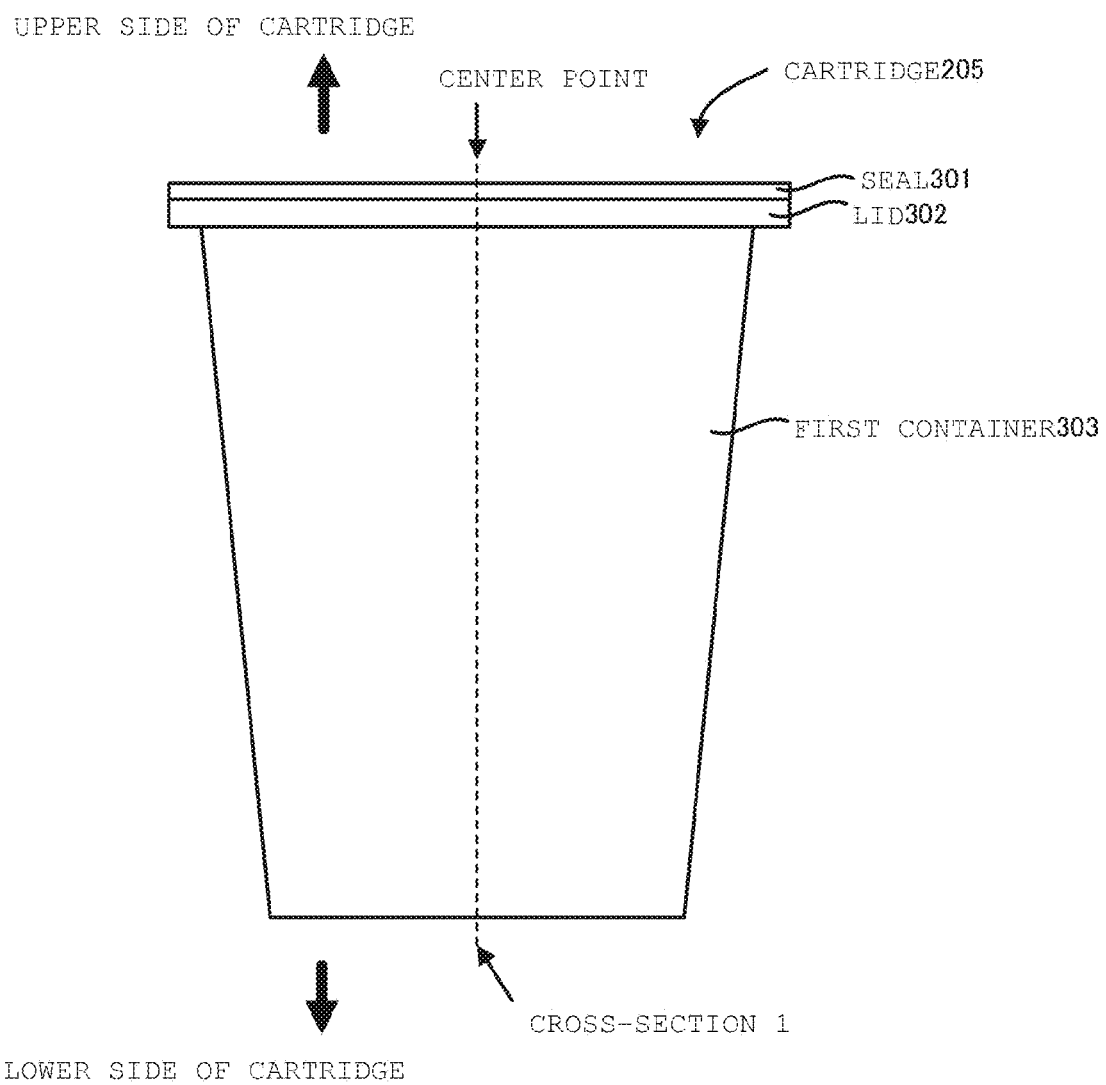
FIG. 3 illustrates a sterilizing agent cartridge used in the sterilization apparatus according to one embodiment when viewed from a side.

Next, the cartridge 205 for a sterilizing agent (hydrogen peroxide solution) to be used in the sterilization apparatus will be described with reference to FIG. 3. In the present exemplary embodiment, it is described that a hydrogen peroxide solution is used as the sterilizing agent. FIG. 3 illustrates the sterilizing agent cartridge 205 used in the sterilization apparatus which is viewed from a side.

The cartridge illustrated in FIG. 3 is a cartridge which may store the sterilizing agent with an amount enough for performing sterilizing processing for a plurality of times in one bottle. In the cartridge illustrated in FIG. 3, a chemical solution, such as hydrogen peroxide, to be used as a sterilizing agent is stored. As illustrated in FIG. 3, the cartridge includes a first container 303, a lid 302 of the first container 303, and a seal 301 on the lid 302.

An external appearance of the first container 303 has a cup shape. A material of the first container 303 is polypropylene (plastic) tolerant to hydrogen peroxide which is the sterilizing agent. In addition, the first container 303 is provided to protect a second container 409 described below.

The lid 302 is a lid for closing the first container 303 at an upper side thereof. In other words, the lid 302 is bonded to a groove at an outer periphery of the first container 303. A material of the lid is polypropylene (plastic) tolerant to hydrogen peroxide which is the sterilizing agent.

The seal 301 includes paper and a double-sided tape, and is attached to the lid 302 with the double-sided tape. Information, such as a brand name, for identifying the cartridge is described on the paper of the seal.

Figure 4:
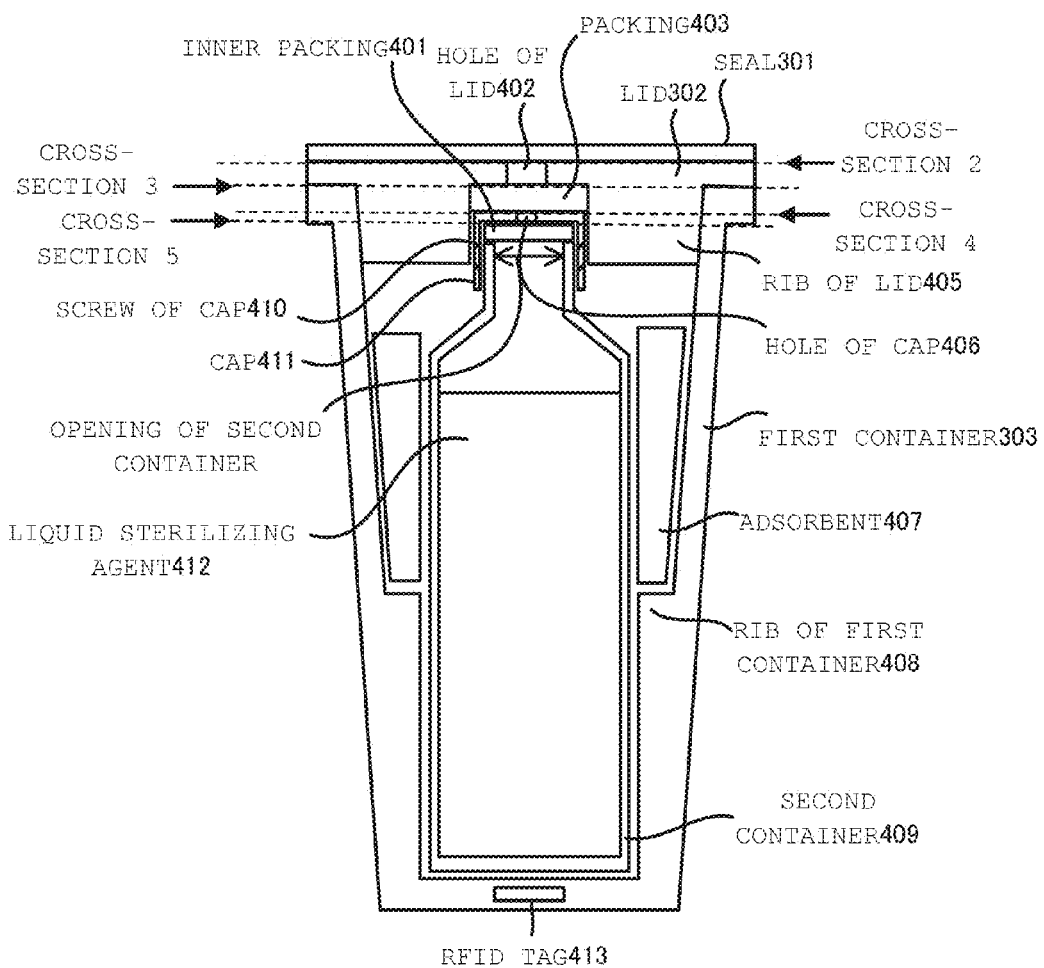
FIG. 4 is a cross-sectional view of a cross-section 1 of the cartridge according to one embodiment.

When viewed from the upper side of the cartridge, a cross-section of the cartridge at a center point of the cartridge is taken as a cross-section 1. Next, an interior structure of the cartridge will be described with reference to FIG. 4. FIG. 4 is a cross-sectional view of the cross-section 1 of the cartridge.

The lid 302 includes a hole 402 at a center point, and the hole 402 is an insertion opening for inserting the extraction needle (injection needle) for suctioning the sterilizing agent in the cartridge into the cartridge from the upper side of the cartridge. The hole 402 is an application example of a second exhaust mechanism.

At least a portion of the exhaust path through which the gas in the cartridge is exhausted to the outside of the cartridge is formed in the lid of the first container with the hole 402 (the second exhaust mechanism) through which the gas exhausted from the second container is exhausted from the first container.

A rib 405 for fixing the second container 409 is provided to the lid 302. As described above, the lid 302 is the lid of the first container, and includes the hole 402 for inserting the extraction needle for extracting the hydrogen peroxide solution by the sterilization apparatus.

A rib 408 for fixing the second container 409 is provided to the first container 303.

As illustrated in FIG. 4, the second container 409 is included in the interior space of the first container 303. In other words, the second container 409 is set within the first container, and is a container into which the sterilizing agent (chemical solution) such as a hydrogen peroxide solution is filled. A liquid sterilizing agent (hydrogen peroxide solution) 412 is filled in the second container 409. A material of the second container 409 is polyethylene (plastic) tolerant to hydrogen peroxide which is the sterilizing agent.

An adsorbent 407 for adsorbing the sterilizing agent 412 is filled in the space between the second container 409 and the first container 303. A material of the adsorbent 407 is vermiculite which is a kind of a mineral ore nonreactive to the sterilizing agent. Instead of the adsorbent 407, a decomposition agent, such as manganese dioxide or activated carbon, which is a catalyst for decomposing the sterilizing agent may be filled. In the adsorbent 407, a decomposition agent which is a material for decomposing the sterilizing agent is also filled in addition to the adsorbent 407.

In this way, the adsorbent for adsorbing a gas exhausted from the second container is filled in the space between the first container and the second container. Further, the decomposition agent for decomposing the gas exhausted from the second container is also filled in the space between the first container and the second container. Thus, the adsorbent and the decomposition agent are filled, and may reduce a possibility of outflow of the harmful chemical solution from the cartridge.

An RF-ID 413 is embedded in the lower portion of the first container 303.

A cap 411 is mounted to an opening of the second container 409. A screw 410 is provided in the interior of the cap 411, thus the cap 411 is fixed by turning the cap 411. That is, the cap 411 is a cap of the second container for sealing the opening of the second container and the inner packing.

The cap 411 includes a hole 406 at a center point, and the hole 406 is an insertion opening for inserting the extraction needle (injection needle) for suctioning the sterilizing agent in the cartridge into the cartridge from the upper side of the cartridge. That is, the hole 406 is a hole for inserting the extraction needle for extracting the hydrogen peroxide solution.

A gap through which a gas may pass but a liquid may not is provided between the cap 411 and the second container 409 to which the cap 411 is fixed.

An inner packing 401 for preventing leakage of the liquid in the second container 409 to the outside is disposed between the opening of the second container 409 and the cap 411. A material of the inner packing 401 is a material having both a waterproof property and moisture permeability.

The packing 401 may be made of, for example, Gore-tex (a brand name of W.L. Gore and Associates, Inc. in the US) made by combining an expanded polytetrafluoroethylene film with a polyurethane polymer. The Gore-tex material has approximately 1.4 billion pores per square centimeter and has a property of passing a gas but not passing a liquid therethrough. Therefore, the gas in the second container 409 is allowed to pass through the space between the first container 303 and the second container 409.

The material for the inner packing used in the sterilizing agent cartridge is not limited to Gore-tex, and may be other waterproof and moisture permeable material. For example, Gore-tex is a porous waterproof and moisture permeable material, but may be a nonporous waterproof and moisture permeable material such as DIAPLEX.

The inner packing 401 is an application example of a first packing. According to one embodiment, the packing includes a filling material (the inner packing 401 and the packing 403) for preventing leakage of the liquid filled in the cartridge.

As described above, at least a portion of the exhaust path for exhausting the gas in the cartridge to the outside thereof is formed in the first packing (the inner packing 401) which has waterproof and moisture permeability properties and is disposed on the opening of the second container. That is, the inner packing 401 is a material which has a property of passing a gas but not passing a liquid therethrough and covers the opening of the second container.

The packing 403 is disposed between the cap 411 and the lid 302. The packing 403 is an application example of a second packing.

A material of the packing 403 is expanded polyethylene used as a shock-absorbing material. The packing 403 is used to absorb size errors of the respective parts such as the lid 302, the cap 411, the second container 409, and the first container 303, and remove the sterilizing agent stuck to the extraction needle (injection needle) when the extraction needle is withdrawn from the cartridge. The packing 403 includes a path for discharging the gas in the first container 303 to the outside.

The packing 403 is pressurized between the lid 302 and the cap 411 and compressed (pressure bonded) to absorb the size errors of the respective parts constituting the cartridge. Therefore, it becomes difficult to pass a gas or a liquid unless there is a gap (a notch) in the packing. Thus, although described below in detail, a notch is provided in the packing 403 used herein, and the gas in the space between the second container 409 and the first container 303 is discharged to the outside. The notch is an application example of a first exhaust mechanism.

As described above, at least a portion of the exhaust path for exhausting the gas in the cartridge to the outside thereof is formed in the packing 403 (the second packing) having the first exhaust mechanism (notch) which is pressure bonded to the first container and exhausts the gas from the second container into the first container.

As illustrated in FIG. 4, the cartridge includes the seal 301, the lid 302, the packing 403, the cap 411, the inner packing 401, the second container 409, and the first container 303 in this order from the upper side of the cartridge, such that they overlap each other. A cross-section 2 is a cross-section between the seal 301 and the lid 302. A cross-section 3 is a cross-section between the packing 403 and the lid 302. A cross-section 4 is a cross-section between the cap 411 and the packing 403. A cross-section 5 is a cross-section between the cap 411 and the inner packing 401.

Figure 5:
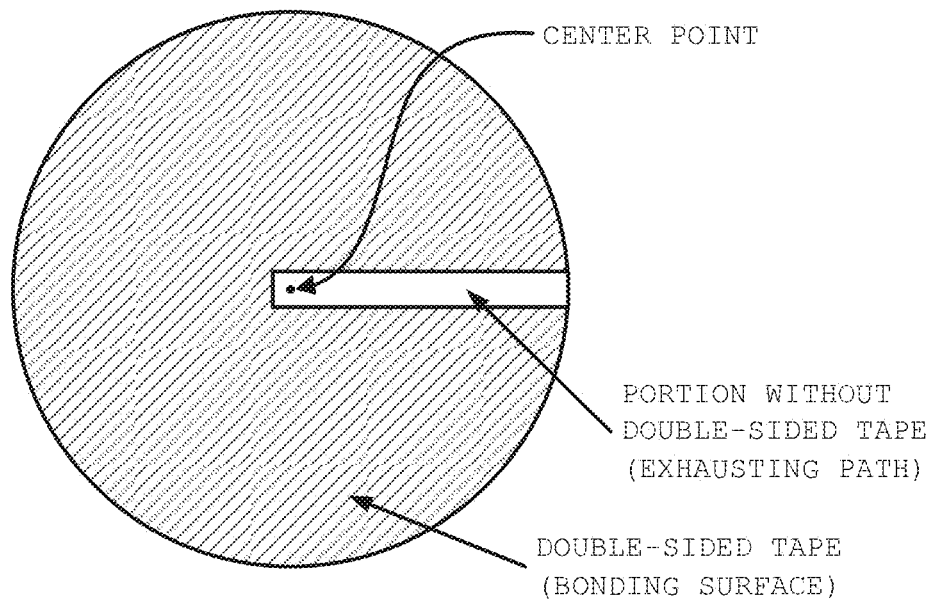
FIG. 5 illustrates a rear surface of a seal when a cross-section 2 is viewed from the lower side of the cartridge according to one embodiment.

Next, a rear surface of the seal 301 when the cross-section 2 is viewed from the lower side of the cartridge will be described with reference to FIG. 5. FIG. 5 illustrates the rear surface of the seal 301 when the cross-section 2 is viewed from the lower side of the cartridge.

As illustrated in FIG. 5, the seal 301 has a circular shape corresponding to a shape of the cartridge. As illustrated in FIG. 5, the rear surface of the seal 301 is a bonding surface to be bonded to the lid 302, and a double-sided tape (adhesive) for bonding is applied to the rear surface of the seal 301. The hatched part illustrated in FIG. 5 represents that the double-sided tape is applied thereto.

In addition, the rear surface of the seal 301 includes a portion without the double-sided tape to which the double-sided tape is not applied, from the center point toward a circumference of the circle of the seal. The portion without the double-sided tape is not bonded to the lid 302 and thus serves as an exhaust path for exhausting the gas in the first container 303 to the outside.

The seal 301 may be bonded to the lid 302, and includes a portion which may not be bonded to the lid 302 (a portion without a double-sided tape) as an exhaust path for exhausting a gas from the position of the hole 402 of the lid. The portion which may not be bonded to the lid 302 (the portion without a double-sided tape) is an application example of a third exhaust mechanism.

The seal 301 may be bonded to the lid 302 of the first container, and is formed as a seal including "a portion which may not be bonded to the lid 302 (a portion without a double-sided tape) (the third exhaust mechanism)", through which the gas exhausted from the hole of the lid 302 of the first container (the second exhaust mechanism) is exhausted from the first container.

In detail, the third exhaust mechanism of the seal 301 is a non-bondable portion (a portion without a double-sided tape) which is not bonded to the lid of the first container and extended from the second exhaust mechanism of the lid of the first container to a periphery of the seal.

Figure 6:
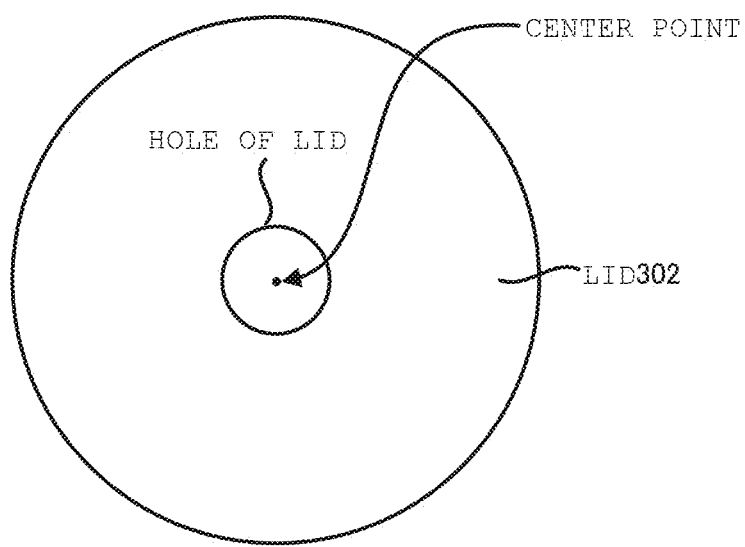
FIG. 6 is a cross-sectional view when the cross-section 2 is viewed from the upper side of the cartridge according to one embodiment.

Next, the cross-section 2 when viewed from the upper side of the cartridge will be described with reference to FIG. 6. FIG. 6 is a cross-sectional view when the cross-section 2 is viewed from the upper side of the cartridge.

As illustrated in FIG. 6, the hole 402 of the lid is formed at a center point of the circular lid 302 corresponding to a shape of the first container 303, and is an insertion opening for inserting the extraction needle (injection needle) for suctioning the sterilizing agent in the cartridge into the cartridge from the upper side of the cartridge.

Figure 7:
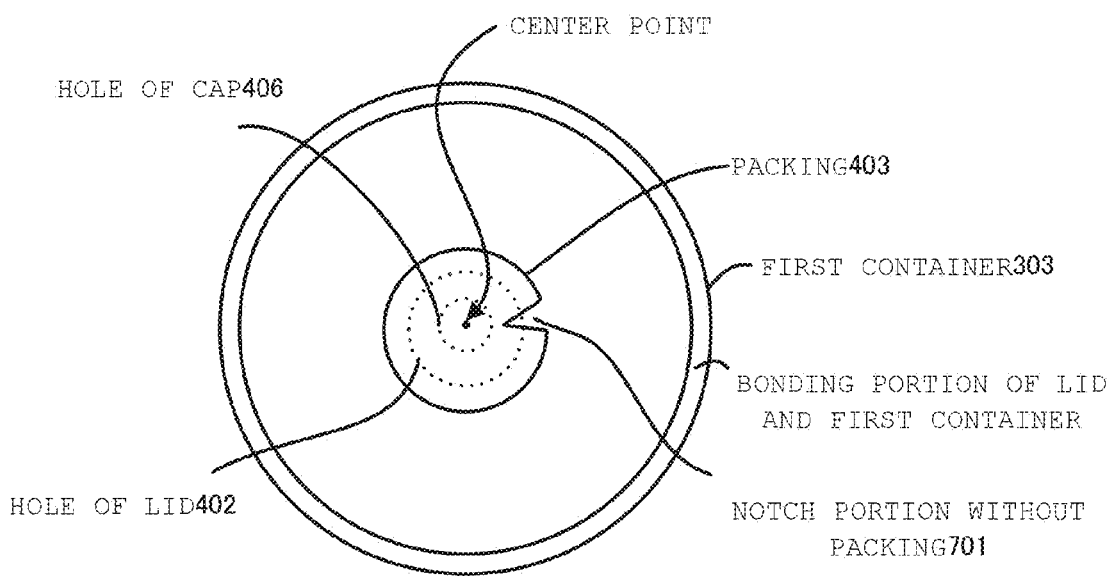
FIG. 7 is a cross-sectional view when a cross-section 3 is viewed from the upper side of the cartridge according to one embodiment.

Next, the cross-section 3 when viewed from the upper side of the cartridge will be described with reference to FIG. 7. FIG. 7 is a cross-sectional view when the cross-section 3 is viewed from the upper side of the cartridge.

The packing 403 is disposed on the circular first container 303 centering around the center point thereof. As illustrated in FIG. 7, the packing 403 has a notch, and there is a portion 701 without the packing. The notch does not reach the hole 406 of the cap but reaches the hole 402 of the lid.

As illustrated in FIG. 7, the hole 402 of the lid is a hole larger than the hole 406 of the cap.

The portion 701 without the packing reaches an area of the portion of the hole 402 of the lid, but does not reach an area of the portion of the hole 406 of the cap (in other words, the area of the portion of the hole 406 is covered with the packing). Thus, the packing 403 includes an exhaust path (the portion 701 without the packing) through which the hole 402 of the lid is communicated with the space between the first container 303 and the second container 409.

As described above, the packing 403 is configured such that the hole 406 of the cap for inserting the extraction needle may not be communicated with the portion 701 without the packing, and thus the gas in the second container 409 may be prevented from passing through the inner packing 401 and being discharged from the hole 406 of the cap. Therefor, if the gas in the second container 409 contains hydrogen peroxide, the gas is prevented from being discharged from the cartridge.

In other words, the hole 402 of the lid is a hole larger than the hole 406 of the cap for inserting the extraction needle, and the exhaust path (the portion 701 without the packing) of the packing 403 has a length between a position of the hole 402 of the lid and a position of the hole 406 of the cap for inserting the extraction needle, from a periphery of the packing 403.

Next, the cross-section 4 when viewed from the upper side of the cartridge will be described with reference to FIG. 8.

Figure 8:
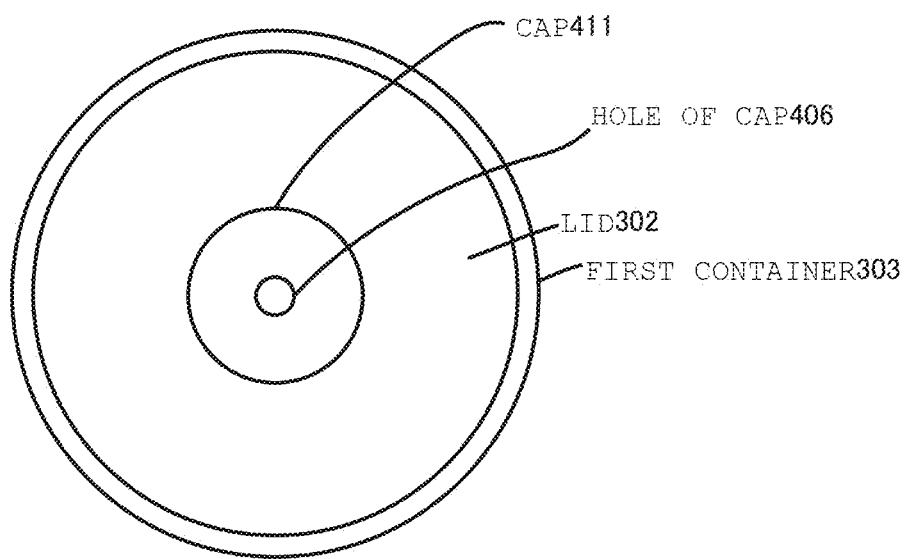
FIG. 8 is a cross-sectional view when a cross-section 4 is viewed from the upper side of the cartridge according to one embodiment.

FIG. 8 is a cross-sectional view when the cross-section 4 is viewed from the upper side of the cartridge.

The hole 406 of the cap is located on the center of the cap 411. The hole 406 of the cap is an insertion opening for inserting the extraction needle (injection needle) for suctioning the sterilizing agent in the cartridge into the cartridge from the upper side of the cartridge.

Figure 9:
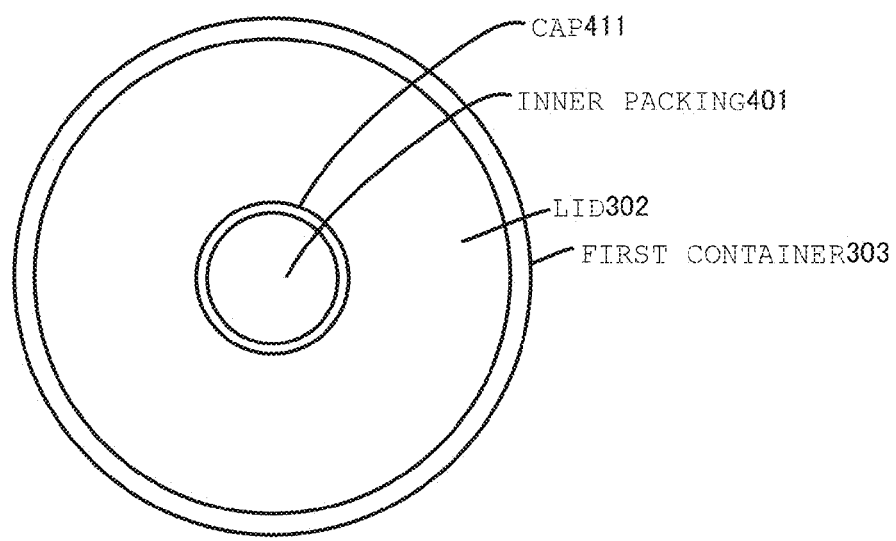
FIG. 9 is a cross-sectional view when a cross-section 5 is viewed from the upper side of the cartridge according to one embodiment.

Next, the cross-section 5 when viewed from the upper side of the cartridge will be described with reference to FIG. 9. FIG. 9 is a cross-sectional view when the cross-section 5 is viewed from the upper side of the cartridge. As illustrated in FIG. 9, the inner packing 401 is disposed between the cap 411 and the opening of the second container 409 to fully cover the opening.

Figure 10:
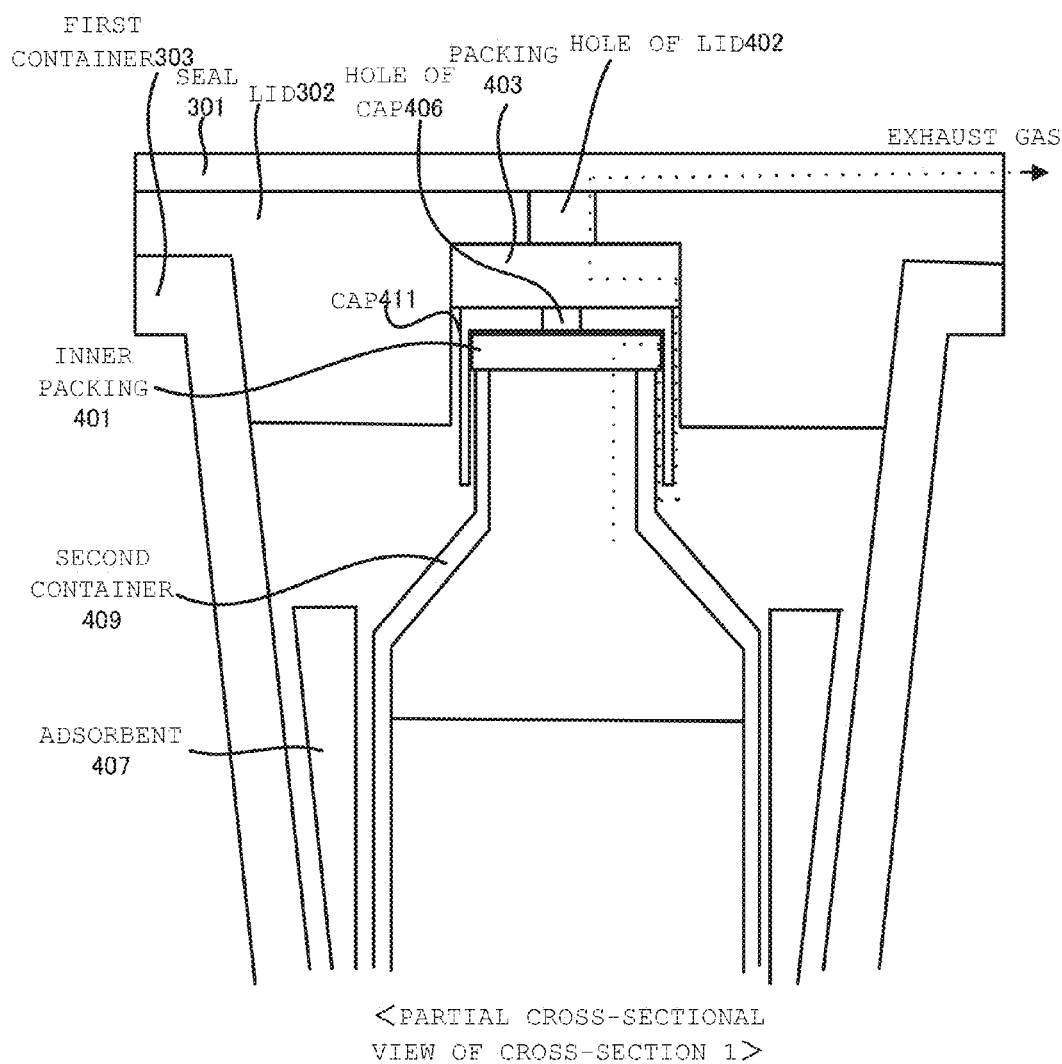
FIG. 10 is an enlarged partial cross-sectional view of the cross-sectional view in FIG. 4 (an upper portion of the cartridge).

Next, a mechanism for discharging the gas in the cartridge to the outside will be described with reference to FIG. 10. FIG. 10 is an enlarged partial cross-sectional view of the cross-sectional view in FIG. 4 (an upper portion of the cartridge).

A dotted line in FIG. 10 indicates a flow of the gas discharged from the second container 409 to the outside. As illustrated in FIG. 10, the gas in the second container 409 passes through the inner packing 401, passes between the cap 411 and the opening of the second container 409, and then reaches the space between the first container 303 and the second container 409.

If the reached gas contains the sterilizing agent (hydrogen peroxide), the sterilizing agent is adsorbed by the adsorbent 407. Further, the adsorbent 407 contains a decomposition agent for decomposing the sterilizing agent, and thus the sterilizing agent contained in the gas is decomposed by the decomposition agent. For example, if the sterilizing agent contained in the gas is hydrogen peroxide, hydrogen peroxide is decomposed into water and oxygen by manganese dioxide as a decomposition agent.

The gas (containing decomposition products, i.e., water and oxygen, by the decomposition agent) having reached the space between the first container 303 and the second container 409 passes through the space between the cap 411 and the lid 302 and reaches the packing 403. The portion 701 without the packing (notch) is provided to an area of the portion of the hole 402 of the lid in the packing 403, and thus the gas having reached the packing 403 passes through the space and is exhausted through the hole 402 of the lid.

In other words, in the packing 403 (second packing), the portion 701 without the packing 403 (notch) (the first exhaust mechanism) is configured to be communicated with the gas between the first container and the second container exhausted from the second container, and the hole of the cover of the first container.

The hole 402 of the lid of the first container is an application example of the second exhaust mechanism.

In detail, the notch (the first exhaust mechanism) of the packing 403 (the second packing) has a length which extends from a portion, where the gas between the first container and the second container exhausted from the second container and the second packing contact with each other (a periphery of the packing 403 or a peripheral valve), to the hole 402 of the lid (the second exhaust mechanism) of the first container, but does not reach the hole 406 of the cap of the second container.

The seal 301 includes the portion without the double-sided tape and the lid 302 is not bonded to the seal 301 at that portion, and thus an exhaust path is formed. Accordingly, the gas exhausted through the hole 402 of the lid passes through the portion without the double-sided tape (the exhaust path) and is discharged to the outside of the cartridge.

As described above, by providing the path for discharging the gas in the cartridge to the outside thereof, an internal pressure in the second container 409 may be prevented from being increased by the water or oxygen generated by decomposing the sterilizing agent (hydrogen peroxide) in the cartridge, and thus the damage of the second container 409 or the leakage of the sterilizing agent from the space between the opening of the second container 409 and the cap 411 may be prevented.

Further, the above-described configuration may reduce a possibility that the pressure in the cartridge is increased by the water or the gas of oxygen (product) generated by decomposing the sterilizing agent (for example, hydrogen peroxide) in the cartridge, and the cartridge is damaged or the sterilizing agent in the cartridge is leaked to the outside thereof.

Figure 11:
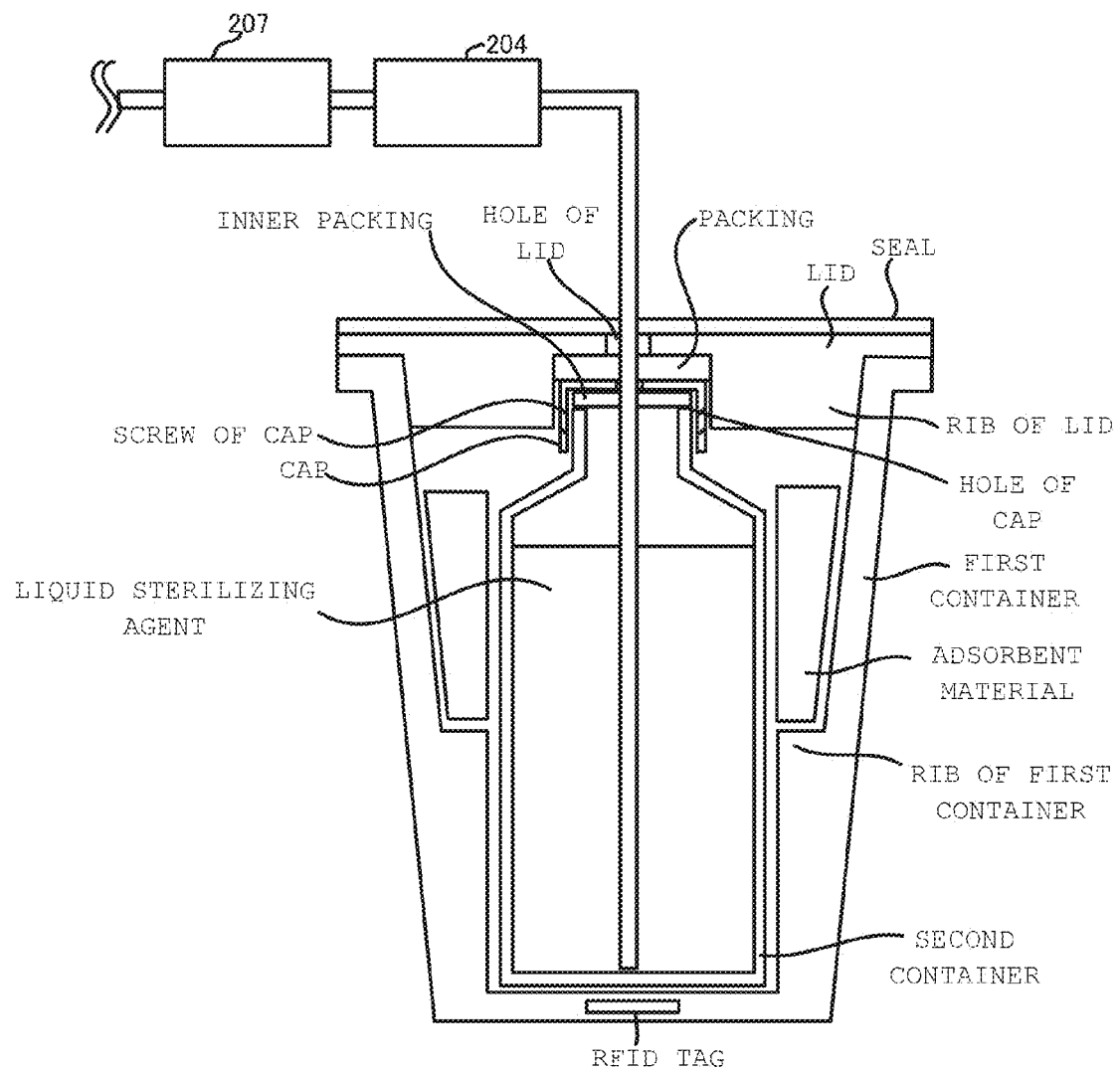
FIG. 11 is a cross-sectional view of the cross-section 1 of the cartridge according to one embodiment.

Next, a structure for inserting into the cartridge the extraction needle (injection needle) for suctioning the sterilizing agent in the cartridge will be described with reference to FIG. 11. FIG. 11 is a cross-sectional view of the cross-section 1 of the cartridge.

When the sterilization apparatus 100 is operated to lower the extraction needle (injection needle) from the upper portion of the cartridge toward the cartridge, the extraction needle (injection needle) is inserted into the hole 402 of the lid and the hole 406 of the cap.

In this case, the seal 301, the packing 403, and the inner packing 401 are penetrated by the injection needle, and the sterilization apparatus 100 is operated such that a tip end of the injection needle comes to a lower portion of the second container 409.

As described above, the seal 301, the packing 403, and the inner packing 401 are made of materials which may be penetrated by the injection needle. In addition, insertion openings are previously provided as the hole of the cap and the hole of the lid to the cap 411 and the lid 302 respectively which may not be easily penetrated by the injection needle.

Second Exemplary Embodiment

A second exemplary embodiment of a sterilizing agent cartridge will be described below with reference to the accompanying drawings. The second exemplary embodiment is different from the first exemplary embodiment only in view of the seal 301. Other configurations of the cartridge are the same as those of the first exemplary embodiment, and thus only the seal 301 of the second exemplary embodiment will be described herein.

Figure 12:
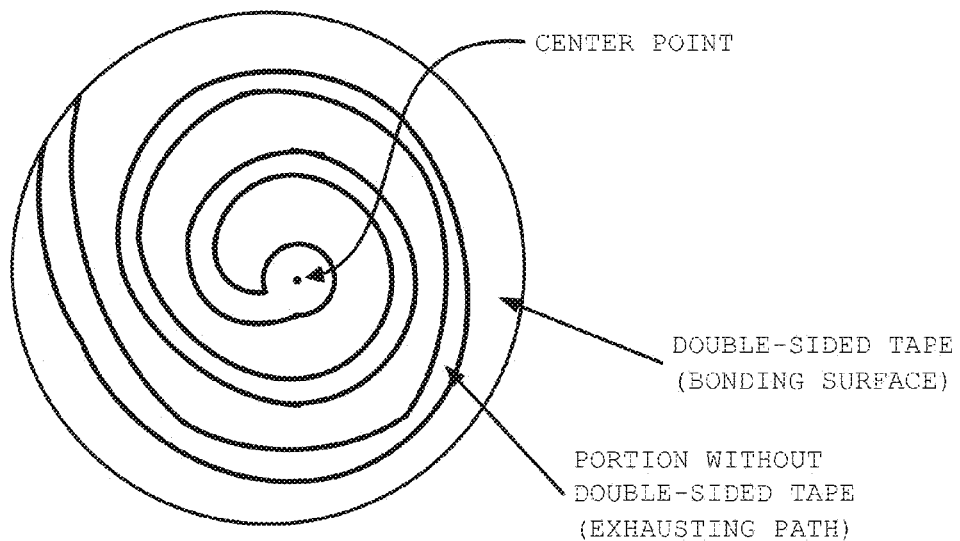
FIG. 12 illustrates the rear surface of the seal when the cross-section 2 is viewed from the lower side of the cartridge according to one embodiment.

Next, the rear surface of the seal 301 when the cross-section 2 is viewed from the lower side of the cartridge will be described with reference to FIG. 12. FIG. 12 illustrates the rear surface of the seal 301 when the cross-section 2 is viewed from the lower side of the cartridge.

As illustrated in FIG. 12, the seal 301 has a circular shape in correspondence to the shape of the cartridge. As illustrated in FIG. 12, the rear surface of the seal 301 is a bonding surface to be bonded to the lid 302, and a double-sided tape (adhesive) for bonding is applied to the rear surface of the seal 301. The double-sided tape (bonding surface) illustrated in FIG. 12 represents that the double-sided tape is applied.

In addition, the rear surface of the seal 301 includes a portion without the double-sided tape to which the double-sided tape is not applied, from the center point toward a circumference of the circle of the seal in a spiral shape. The portion without the double-sided tape is not bonded to the lid 302 and thus serves as an exhaust path for exhausting the gas in the first container 303 to the outside.

The seal 301 may be bonded to the lid 302, and includes a portion which may not be bonded to the lid 302 (a portion without a double-sided tape) as an exhaust path for exhausting a gas from the position of the hole 402 of the lid. The portion which may not be bonded to the lid 302 (the portion without a double-sided tape) is an application example of the third exhaust mechanism.

In detail, the third exhaust mechanism of the seal 301 is a non-bondable portion (a portion without a double-sided tape) which is not bonded to the lid of the first container and extended from the hole (the second exhaust mechanism) of the lid of the first container to a periphery of the seal in a spiral shape.

As illustrated in FIG. 12, the double-sided tape is not applied to the portion without the double-side tape in a spiral shape from the center point toward the circumference of the circle of the seal. Therefore, if the liquid of the sterilizing agent stored in the second container is leaked from the second container and further leaked from the space between the first container and the second container via the portion 701 where the second packing is cut off and removed, and from the hole 402 of the lid to the outside of the cartridge, the leakage of the liquid of the sterilizing agent to the outside of the cartridge may be stopped along the way of the spiral exhaust path. Thus, a possibility that the liquid of the sterilizing agent stored in the cartridge is leaked to the outside of the cartridge may be reduced.

Further, although the cartridge according to the above-described first and second exemplary embodiments is described to be used in a sterilization apparatus, the cartridge of the above-described first and second exemplary embodiments may be used in, for example, a semiconductor manufacturing apparatus. As described above, a chemical solution, for example a hydrogen peroxide solution or the like, is stored in the cartridge used in the semiconductor manufacturing apparatus, and the chemical solution may be suctioned from the cartridge and used in the semiconductor manufacturing apparatus.

As described above, a cartridge capable of reducing a possibility of leakage of a hydrogen peroxide solution may be provided with respect to the cartridge filled with the hydrogen peroxide solution to be used in the sterilization apparatus.

Further, it is possible to reduce a fear of causing damage of the cartridge or leakage of a liquid therefrom due to increase of the pressure in the cartridge. Furthermore, even if the cartridge is damaged, for example, due to a drop of the cartridge, it is possible to reduce a fear that a sterilizing liquid in the cartridge is leaked.

While the disclosure has been described with reference to exemplary embodiments, it is to be understood that the disclosure is not limited to the disclosed exemplary embodiments. The scope of the following claims is to be accorded the broadest interpretation so as to encompass all modifications, equivalent structures, and functions.

This application claims priority from Japanese Patent Application No. 2011-222384 filed Oct. 6, 2011, and Japanese Patent Application No. 2012-147388 filed Jun. 29, 2012, which is hereby incorporated by reference herein in its entirety.

What is claimed is:

1. A cartridge capable of storing a chemical solution, comprising:
   a first container;
   a lid of the first container;
   a second container installed within the first container and configured to store the chemical solution;

a first packing provided at an opening of the second container and configured to prevent the chemical solution stored in the second container from leaking, the first packing exhausting a gas generated by the chemical solution stored in the second container therefrom to a space between the second container and the first container and not passing the chemical solution stored in the second container therethrough; and a second packing positioned directly above the first packing and provided at an interior of the lid of the first container, wherein an exhaust path for allowing the gas, which has been exhausted from an interior of the second container to the space between the second container and the first container through the first packing, to be exhausted to an exterior of the first container is formed in the lid of the first container and in the second packing.

2. The cartridge according to claim 1, wherein the exhaust path includes a first exhaust mechanism provided at the second packing and a second exhaust mechanism provided at the lid of the first container, wherein the first exhaust mechanism is formed in the second packing so as to enable the space between the second container and the first container to be communicated with the second exhaust mechanism, and wherein the second exhaust mechanism is formed in the lid of the first container so as to enable the first exhaust mechanism to be communicated with the exterior of the first container.

3. The cartridge according to claim 1, further comprising a cap of the second container, the cap being provided between the first packing and the second packing, wherein the second packing is pressurized between the lid of the first container and the cap, and wherein the cap is configured to exhaust the gas, which has been exhausted from an interior of the second container through the first packing, to the space between the second container and the first container through a space between the cap and the second container.

4. The cartridge according to claim 1, further comprising, in the space between the first container and the second container, an adsorbent for adsorbing a gas of a medical agent included in the chemical solution, the gas being exhausted, through the first packing, from the interior of the second container to the space between the first container and the second container.

5. The cartridge according to claim 1, further comprising, in the space between the first container and the second container, a decomposition agent for decomposing a gas of a medical agent included in the chemical solution, the gas having been exhausted, through the first packing, from the interior of the second container to the space between the first container and the second container.

6. The cartridge according to claim 3, wherein the cap is provided at an opening of the second container and configured to exhaust the gas which has been exhausted from the interior of the second container through the first packing to the space between the second container and the first container through the space between the cap and the second container and not to pass the chemical solution stored in the second container therethrough.

7. The cartridge according to claim 1, wherein the first packing is a packing having waterproof and moisture permeability properties.

8. The cartridge according to claim 2, further comprising a cap having an insertion opening for inserting a tube for extracting the chemical solution stored in the second container, the cap being a cap of the second container and is provided at the opening of the second container, wherein the first exhaust mechanism is formed in the second packing so as to enable the space between the second container and the first container to be communicated with the second exhaust mechanism and not to enable the space between the second container and the first container to be communicated with the insertion opening of the cap.

9. The cartridge according to claim 8, wherein the second exhaust mechanism is also an insertion opening in which the tube for extracting the chemical solution stored in the second container is inserted.

10. The cartridge according to claim 9, wherein the insertion opening provided as the second exhaust mechanism is larger than the insertion opening provided in the cap, and wherein the first exhaust mechanism made in the second packing is in the form of a notch having a length which enables the space between the second container and the first container to be communicated with the second exhaust mechanism and does not enable the space between the second container and the first container to be communicated with the insertion opening of the cap.

11. The cartridge according to claim 2, further comprising a seal bondable to the lid of the first container, wherein the seal includes a third exhaust mechanism for exhausting a gas exhausted from the second exhaust mechanism of the lid of the first container from an interior of the first container to the exterior of the first container.

12. The cartridge according to claim 11, wherein the third exhaust mechanism of the seal is a non-bondable portion which is not bonded to the lid of the first container from the second exhaust mechanism to a periphery of the seal.

13. The cartridge according to claim 11, wherein the third exhaust mechanism of the seal is a non-bondable portion which is in a spiral shape and which is not bonded to the lid of the first container from the second exhaust mechanism to a periphery of the seal.

14. The cartridge according to claim 1, wherein the chemical solution is a sterilizing agent for sterilizing a target object for sterilization, and wherein the cartridge is a cartridge to be used in a sterilization apparatus configured to perform sterilizing processing using the sterilizing agent.

15. The cartridge according to claim 1, wherein the chemical solution is a hydrogen peroxide solution.

* * * * *